United States Patent
Shiraki et al.

(10) Patent No.: US 6,566,064 B1
(45) Date of Patent: May 20, 2003

(54) METHOD FOR ANTICIPATING SENSITIVITY TO MEDICINE FOR OSTEOPOROSIS

(75) Inventors: Masataka Shiraki, Misato-mura (JP); Yasuyoshi Ouchi, Tokyo-to (JP); Takayuki Hosoi, Tokyo-to (JP); Nobutaka Kusaba, Osaka (JP); Toshiaki Baba, Osaka (JP); Hiroshi Yoshida, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/572,891

(22) Filed: May 18, 2000

(30) Foreign Application Priority Data

May 18, 1999 (JP) .............................. 11-136653
Jun. 11, 1999 (JP) .............................. 11-165642

(51) Int. Cl.[7] .......................... C12Q 1/68; C07H 21/04
(52) U.S. Cl. ........................................ 435/6; 536/23.5
(58) Field of Search .......................... 435/6; 536/23.5, 536/24.31, 24.33

(56) References Cited

PUBLICATIONS

Langdahl, B.L. et al. Ernst Schering Res. Found. Workshop 25(Novel Approaches to Treatment of Osteoporosis):83–101 (1998).*
Deng, H.W. et al. Human Genetics 103(5):576–585 (Nov. 1998).*
Efstathiadou, Z. et al. Osteoporosis International 12(4):326–331 (2001).*
Aerssens, J. et al. Osteoporosis International 11(7):583–591 (2000).*
Shiraki, M. et al. Journal of Bone and Mineral Density 12(9): 1438–1445 (1997).*
Heikkinen, A.M. et al. Maturitas 34(1):33–41 (Jan. 2000).*

* cited by examiner

Primary Examiner—Carla J. Myers
Assistant Examiner—Diana Johannsen
(74) Attorney, Agent, or Firm—Kubovcik & Kubovcik

(57) ABSTRACT

A method for anticipating sensitivity to a medicine for osteoporosis is provided which is characterized by analyzing respective genetic polymorphisms of a vitamin D receptor gene, an estrogen receptor gene, and an apolipoprotein E gene from a genome DNA contained in a sample obtained from a human, and anticipating, based on the analyzed combination of the genetic polymorphisms, that the sample is derived from an individual who shows a specific priority to sensitivities to a plurality of remedies for osteoporosis. A reagent for simultaneously detecting genetic polymorphisms is also provided which contains amplification primers and/or detection probes specific to respective genes of the vitamin D receptor gene, apolipoprotein E gene, and estrogen receptor gene. Further, a method for simultaneously detecting these genes, and a method for selecting remedies for bone disease based on the genetic polymorphisms are provided. According to the method of the present invention, a diagnosis as to which remedy, or medicine, for osteoporosis a subject patient has higher sensitivity can be made before the administration of the medicine so that selection of an appropriate medicine is possible and the QOL (quality of life) of the patient can be improved.

1 Claim, 6 Drawing Sheets

|  |  | VDR | ApoE | ER |
|---|---|---|---|---|
| Blank |  | ... | ... | ... |
| No. 1 |  | Bb | 3/4 | xx |
| No. 2 |  | BB | 3/3 | Xx |
| No. 3 |  | bb | 4/4 | XX |

VDR side

BB

Bb bb

ApoE side

4(+)

or

4(-)

ER side

| | | VDR | ApoE | ER |
|---|---|---|---|---|
| Blank | | ... | ... | ... |
| No. 1 | | Bb | 3/4 | xx |
| No. 2 | | BB | 3/3 | Xx |
| No. 3 | | bb | 4/4 | XX |

Fig. 5

| | | ApoE |
|---|---|---|
| Blank | | - - - |
| No. 1 | | 3/4 |
| No. 2 | | 3/3 |
| No. 3 | | 4/4 |

METHOD FOR ANTICIPATING SENSITIVITY TO MEDICINE FOR OSTEOPOROSIS

FIELD OF THE INVENTION

The present invention relates to a novel method for the analysis of human-derived samples that can provide information useful in the therapy of osteoporosis. Specifically, the present invention relates to a method for the analysis of genetic polymorphism of genome DNA in human-derived samples in order to anticipate which is the most effective remedy for osteoporosis, in particular, among vitamin D, estrogen, and vitamin K2. Also, the present invention relates to a method for anticipating, based on a combination of genetic polymorphisms of genome DNA in a human-derived sample, that the sample is derived from an individual who shows specified priority in sensitivity to the above medicines. Further, the present invention relates to a kit for the analysis of genetic polymorphisms that can be used in the above method.

BACKGROUND OF THE INVENTION

Osteoporosis is the state of a disease in which bone mass (the amount of minerals, mainly calcium contained in bone) decreases and the fine structure of bone tissue changes so that the bone becomes brittle and tends to be broken. It occurs mostly in females after menopause and in senior males. It is said that the number of patients with osteoporosis is presumably 10,000,000 in Japan. It is anticipated that as the ratio of elderly persons in the population increases, the number of patients will henceforth inevitably increase.

At present, various medicines such as bone activators, e.g., calcium preparations, vitamin D, etc., bone resorption depressants, e.g., estrogen, etc., and osteogenesis accelerators, e.g., vitamin K, etc., are used to treat osteoporosis. However, their therapeutical effects vary randomly depending on the patient and there have been made almost no study as to how to use a right medicine with a right patient. Since it has been taken as a rule that these remedies are administered singly, there is currently no way other than actually administering a single medicine to patients for several years and obtaining results before it can be judged based on the results which medicine is most effective. This is extremely inefficient.

On the other hand, recent studies on genes have suggested a relationship between some genetic polymorphisms and the sensitivity of a patient to remedies for osteoporosis. For example, there is a report that the genotype A that is not cleaved with Apa I in the intron region between exon 8 and exon 9 of the vitamin D receptor (hereafter, referred to as VDR) gene is more sensitive to vitamin D than the genotype a that is cleaved with the same restriction enzyme [see, for example, JP-A-8-126497 and JP-A-8-126500].

Also, Shiraki et al. [Resume of 1997 Conference of Japanese Society for Bone and Mineral Research, page 52] describe that in accordance with the results of examinations on the relationships between the polymorphism of VDR gene and sensitivity to vitamin D, between the polymorphism of estrogen receptor (hereafter, referred to as ER) gene and sensitivity to estrogen, and between the polymorphism of apolipoprotein E (hereafter, referred to as ApoE) gene and sensitivity to vitamin K2, the VDR genotype AAB (B being a genotype that is not cleaved with Bsm I in the intron region between exon 8 and exon 9) is significantly lower in sensitivity to vitamin D than aabb. Also, the ER genotype PpXx (P and X being genotypes that are not cleaved with Pvu II and Xba I, respectively) is significantly higher in sensitivity to estrogen than other genotype groups, and the ApoE4(+) group is significantly lower in sensitivity to vitamin K2 than the ApoE4(−) group.

Further, it is described that the genotype group whose Restriction Fragment Length Polymorphism (RFLP) pattern obtained by cleaving the vitamin D-binding protein (DBP) gene with Hae III and Sty I is of the GC2-2 type is higher in sensitivity to vitamin D than the other groups [JP-A-8-201373].

However, each of these results is used to anticipate sensitivity to one medicine based on the polymorphism of one gene and enable nothing other than anticipating whether one genotype is higher in sensitivity than other genotypes with respect to one medicine. In other words, it is anticipated that those persons whose VDR genotype is aabb and whose ApoE genotype is ApoE4(−) are higher in sensitivities to vitamin D and vitamin K2, respectively, than those persons who have other VDR and ApoE genotypes. However, it cannot be anticipated which one of vitamin D and vitamin K2 is to be administered to patients having such genotypes in order to obtain a higher therapeutic effect. Therefore, ultimately, to know to which one of different medicines a patient has higher sensitivity, there has been no other way than to administer to the patient one single medicine after another in a span of several years for each medicine and to look at the results. In particular, estrogen not only has a great therapeutic effect but also has a great side effect so that there has been a fear that long-term administration of it to patients could significantly deteriorate their QOL (Quality of Life).

Therefore, an object of the present invention is to provide a means for anticipating to which one of a plurality of remedies for osteoporosis a patient suffering from osteoporosis or a person who has the possibility of acquiring osteoporosis in the future has a higher sensitivity, thereby avoiding progress of the disease caused by long-term administration of a medicine having a low therapeutic effect so that the QOL of patients can be improved.

The present inventors have made intensive research with a view to achieving the above object and as a result they have found that analysis of a human-derived sample containing genome DNA for polymorphisms of the VDR gene, ER gene and ApoE gene makes it possible to anticipate the sensitivity of the human to one of the medicines, vitamin D, estrogen and vitamin K2, that is higher than to the other two medicines based on the combination of the resulting polymorphisms.

That is, they have found a tendency that in the case where a person has both a VDR genotype that is higher in sensitivity to vitamin D than the other genotypes and an ER genotype that is higher in sensitivity to estrogen than the other genotypes, the person is more sensitive to estrogen than vitamin D.

Further, it was found that in the case where a person has an ER genotype that is higher in sensitivity to estrogen than the other genotypes and an ApoE genotype that is higher in sensitivity to vitamin K2 than the other genotypes, the person is more sensitive to estrogen than vitamin K2, and in the case where a person has a VDR genotype that is higher in sensitivity to vitamin D and an ApoE genotype that is higher in sensitivity to vitamin K2, the person is more sensitive to vitamin K2 than vitamin D, thus having arrived at the present invention. In this embodiment, an ApoE genotype is classified into apolipoprotein E4 allele (+) which includes 2/4 3/4 and 4/4, and apolipoprotein E4 allele (−)

which includes 2/2, 2/3 and 3/3, and the ApoE genotype that is higher in sensitivity to vitamin K2 refers to the latter group.

Further, the present inventors also have found that in a case where a person has an apolipoprotein E3 allele (+) 3/3 type, the person is more sensitive to vitamin K2 compared with a case where the person has an apolipoprotein E3 allele (−) (which allele includes all but the 3/3 type). Among apolipoprotein E3 alleles, the order of sensitivity of the alleles to vitamin K2 is 3/3>2/3 or 3/4>2/2, 2/4 or 4/4.

It has been found that in the case where a person has an ER genotype that is higher in sensitivity to estrogen than the other genotypes and an ApoE genotype that is higher in sensitivity to vitamin K2 than the other genotypes, the person is more sensitive to estrogen than vitamin K2, and in the case where a person has a VDR genotype that is higher in sensitivity to vitamin D and an ApoE genotype that is higher insensitivity to vitamin K2, the person is more sensitive to vitamin K2 than vitamin D, thus having arrived at the present invention. In this embodiment, an ApoE genotype is classified into apolipoprotein E3 allele (+) which includes the 3/3 type, and apolipoprotein E3 allele (−) which includes the 2/2, 2/3, 2/4, 3/4 and 4/4, types and the ApoE genotype that is higher in sensitivity to vitamin K2 refers to the former group.

SUMMARY OF THE INVENTION

That is, the embodiments of the present invention are as follows.

1. A method for anticipating sensitivity to a medicine for osteoporosis, characterized by analyzing respective genetic polymorphisms of a vitamin D receptor gene, an estrogen receptor gene, and an apolipoprotein E gene from a genome DNA contained in a sample obtained from a human, and anticipating, based on a combination of the genetic polymorphisms, that the sample is derived from an individual who shows a specific priority of sensitivities to a plurality of remedies for osteoporosis.

The above method is characterized in that the combination of genetic polymorphisms of the vitamin D receptor gene, estrogen receptor gene, and apolipoprotein E gene is one selected from the group consisting of [B(−) X(−) 4(−)], [B(−) X(−) 4(+)], [(B(−) X(+) 4(−)], [B(−) X(+) 4(+)], [B(+) X(−) 4(−)], [B(+) X(−) 4(+)], [B(+) X(+) 4(−)], and [B(+) X(+) 4(+)] (wherein "B" represents a vitamin D receptor allele that is not cleaved with Bsm I in an intron region between exon 8 and exon 9, "X" represents an estrogen receptor allele that is not cleaved with Xba I in an intron region between exon 1 and exon 2, "4" represents an apolipoprotein E4 allele, and (+) and (−) indicate the presence and absence, respectively, of the allele).

The above method is also characterized in that the combination of genetic polymorphisms of the vitamin D receptor gene, estrogen receptor gene, and apolipoprotein E gene is one selected from the group consisting of [B(−) X(−) 3(−)], [B(−) X(−) 3(+)], [B(−) X(+) 3(−)], [B(−) X(+) 3(+)], [B(+) X(−) 3(−)],[B(+) X(−) 3(+)], [B(+) X(+) 3(−)], and [B(+) X(+) 3(+)](wherein "B" represents a vitamin D receptor allele that is not cleaved with Bsm I in an intron region between exon 8 and exon 9, "X"represents an estrogen receptor allele that is not cleaved with Xba I in an intron region between exon 1 and exon 2, "3" represents an apolipoprotein E3 allele, and 3(+) indicates 3/3 type and 3(−) indicates genotypes other than 3/3 type of the allele).

2. A reagent for simultaneously detecting genetic polymorphism of a vitamin D receptor (hereinafter, VDR) gene, an apolipoprotein E (hereinafter, ApoE) gene, and an estrogen receptor (hereinafter, ER) gene, comprising amplification primers specific to the respective genes of VDR, ApoE and ER and detection probes for detecting a VDR genetic polymorphism, an ApoE genetic polymorphism, and an ER genetic polymorphism, respectively.

In the reagent for simultaneously detecting genetic polymorphism of VDR, ApoE and ER genes as described above, the genetic polymorphism of the VDR gene is a Bsm I restriction enzyme fragment length polymorphism BB, Bb or bb on intron 8 of the VDR gene, the genetic polymorphism of the ApoE gene is a Hha I restriction enzyme fragment length polymorphism 2/2, 2/3, 2/4, 3/3, 3/4 or 4/4 of the ApoE gene, and the genetic polymorphism of the ER gene is a Xba I restriction enzyme fragment length polymorphism XX, Xx or xx on intron 1 of the ER gene.

3. A gene amplification reagent for amplifying VDR, ApoE, and ER genes, comprising amplification primers (1) and (2) specific to the VDR gene, amplification primers (3) and (4), or (5) and (6) specific to the ApoE gene, and amplification primers (7) and (8), or (7) and (9) specific to the ER gene as described below.

Amplification primers specific to the VDR gene:

gtgcaggcga ttcggtaggg   20   (SEQ ID NO: 1) and ccagcggaag aggtcaaggg   20   (SEQ ID NO: 2)

Amplification primers specific to the ApoE gene:

ctgggcgcgg acatgg        16   (SEQ ID NO: 3) and cccggcctgg tacact        16   (SEQ ID NO: 4), or ctgggcgcgg acatggagga    20   (SEQ ID NO: 5) and cccggcctgg tacactgcca    20   (SEQ ID NO: 6), Amplification primers specific to the ER gene:

gttccaaatg tcccagccgt    20   (SEQ ID NO: 7) and cctgcaccag aatatgtacc    20   (SEQ ID NO: 8), or gttccaaatg tcccagccgt    20   (SEQ ID NO: 7) and cctgcaccag aatatgttac c  21   (SEQ ID NO: 9)

4. A reagent for simultaneously detecting genetic polymorphisms that can measure VDR, ApoE and ER genetic polymorphisms, comprising detection probes (10) and (11) for detecting a VDR genetic polymorphism, detection probes (12) and (13) for detecting an ApoE genetic polymorphism, and probes (14) and (15), or (16) and (17) for detecting an ER genetic polymorphism.

Detection probes for detecting a polymorphism of VDR gene:

caggcctgcg cattcc        16   (SEQ ID NO:10)

caggcctgca cattcc        16   (SEQ ID NO:11)

Detection probes for detecting a polymorphism of ApoE gene:

aggacgtgcg cggc          14   (SEQ ID NO:12)

```
    aggacgtgtg cggcc      15     (SEQ ID NO:13)
```

Detection probes for detecting a polymorphism of ER gene:

```
    gtgtggtcta gagttg      16     (SEQ ID NO: 14) and gtgtggtctg gagttg      16     (SEQ ID NO: 15), or tctggagttg ggatga      16     (SEQ ID NO: 16) and gtggtctaga gttggg      16     (SEQ ID NO: 17)
```

5. A reagent for simultaneously detecting genetic polymorphisms that can measure VDR, ApoE and ER genetic polymorphisms, comprising detection probes (10) and. (11) for detecting a VDR genetic polymorphism, and detection probes (12), (13), (18) and (19) for detecting an ApoE genetic polymorphism, and detection probes (14) and (15), or (16) and (17) for detecting an ER genetic polymorphism. Detection probes for detecting a polymorphism of VDR gene:

```
    caggcctgcg cattcc      16     (SEQ ID NO: 10) and caggcctgca cattcc      16     (SEQ ID NO: 11)
```

Detection probes for detecting a polymorphism of ApoE gene:

```
    aggacgtgcg cggc        14     (SEQ ID NO: 12)

aggacgtgtg cggcc       15     (SEQ ID NO: 13)

cagaagcgcc tggcag      16     (SEQ ID NO: 18) and cagaagtgcc tggcag      16     (SEQ ID NO: 19)
```

Detection probes for detecting a polymorphism of ER gene:

```
    gtgtggtcta gagttg      16     (SEQ ID NO: 14) and gtgtggtctg gagttg      16     (SEQ ID NO: 15), or tctggagttg ggatga      16     (SEQ ID NO: 16) and gtggtctaga gttggg      16     (SEQ ID NO: 17)
```

6. A method for selecting a remedy for a bone-associated disease characterized by relating a combination of genetic polymorphism of VDR, ApoE and ER genes detected by the above mentioned method for detecting genetic polymorphisms of VDR, ApoE and ER genes to a remedy for a bone-associated disease.

BRIEF DESCRIPTION OF THE DRAWINGS

FIG. 3 is a diagram illustrating the results of detection of VDR, ApoE and ER genetic polymorphisms on one solid phase carrier in the samples amplified by the method of the present invention.

FIG. 5 is a diagram illustrating the results of discrimination of the genetic polymorphism on the samples of Example 5, using a commercially available ApoE gene detection reagent (trade name: INNO-LIPA ApoE, manufactured by Innogenetics Corp.) for ApoE gene only.

EMBODIMENTS OF THE INVENTION

Figure 1:
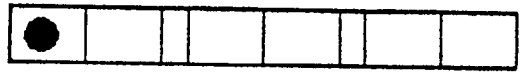
FIG. 1 is a schematic diagram illustrating the results in the case where VDR, ApoE and ER genes are detected on a solid phase carrier to show genetic polymorphism of the respective genes.
Figure 1:
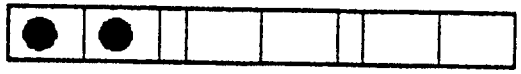
Figure 1:
Figure 1:
Figure 1:
Figure 1:
Figure 1:
Figure 1:
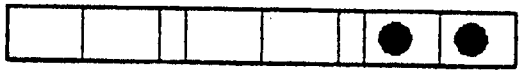
Figure 1:

As used herein, the terminology "anticipating" is intended to mean the ability to predict or diagnose to which of certain medicines for treatment of osteoporosis, if any, a human has the highest sensitivity as compared to sensitivity of the human to the other medicines.

The human-derived sample that can be subjected to the analytical method of the present invention is not particularly limited so far as it contains human genome DNA. Preferably, genome DNAs isolated from various human cells are exemplified. Extraction of genome DNA may be performed by conventional methods such as an SDS/phenol method, a guanidine thiocyanate method, and a CTAB method. Also, those cells and tissues that are readily available and have hitherto been used as template DNA samples for a PCR method, such as whole blood, fractionated blood cells, epidermal cell and mucosa cells used as an abrasive material, or hair may preferably be used. In this case, the cells are homogenized by boiling cells/tissues in water or heating them in an alkali solution to obtain a genome DNA sample.

The analytical method of the present invention is characterized by examining genetic polymorphisms of a VDR gene, an ER gene, and an ApoE gene.

The VDR gene exists on the 12th chromosome. One of the polymorphisms of the VDR gene is detected by whether or not cleavage is possible with restriction enzyme Bsm I in an intron region between exon 8 and exon 9. Assuming that "B" represents the allele that is not cleaved with Bsm I and "b" represents the allele that is cleaved with this restriction enzyme, the VDR genetic polymorphisms can be of three genotypes, i.e., BB, Bb and bb. In the present invention, the VDR genetic polymorphisms are classified into a genotype B(+) having the allele B (that is, BB and Bb) and a genotype B(−) having no allele B (that is, bb). The polymorphism site of the VDR gene means the Bsm I restriction site (GAATGC) in the intron region between exon 8 and exon 9 of the allele b and the site of the allele B corresponding thereto (GAATGT).

The ER gene exists on the 6th chromosome. One of the polymorphisms of the ER gene is detected by whether or not cleavage is possible with restriction enzyme Xba I in an intron region between exon 1 and exon 2. Assuming that "X" represents the allele that is not cleaved with Xba I and "x" represents the allele that is cleaved with this restriction enzyme, the ER genetic polymorphisms can be of three genotypes, i.e., XX, Xx and xx. In the present invention, the ER genetic polymorphisms are classified into a genotype X(+) having the allele X (that is, XX and Xx) and a genotype X(−) having no allele X (that is, xx). The polymorphism site of the ER gene means the Xba I restriction site (TCTAGA) in the intron region between exon 1 and exon 2 of the allele x and the site of the allele X corresponding thereto (TCCAGA).

The ApoE gene exists on the 19th chromosome and consists of four exons and three introns, coding for a protein consisting of 299 amino acids. The ApoE protein participates in the transportation of triglycerides or cholesterols by lipoproteins and is a transfer protein for vitamin K2. The ApoE protein is known to have three isoforms (E2, E3, and E4). Among them, E3 is considered to be of wild type (112th amino acid is cysteine and 158th amino acid is arginine). E4 is the one in which 112th cysteine (codon: TGC) has been substituted by arginine (codon: CGC). E2 is the one in which 158th arginine has been substituted by cysteine. Therefore, ApoE4 allele is cleaved with restriction enzyme Hha I in the mutation site (112th amino acid) while the ApoE2 and ApoE3 alleles are not cleaved with this restriction enzyme in that site (112th amino acid). That is, ApoE4 allele is cleaved in the codon coding 112th arginine, which is a mutation site with Hha I, but ApoE2 or ApoE3 allele is not cleaved in the codon coding 112th cysteine. Further, ApoE3 or ApoE4 allele is cleaved in the codon coding 158th arginine with Hha I, but ApoE 2 allele is not cleaved in the codon coding 158th cysteine, which is a mutation site. They are summarized as below.

|  | 112th amino acid | 158th amino acid |
| --- | --- | --- |
| ApoE2 allele | not cleaved | not cleaved |
| ApoE3 allele | not cleaved | cleaved |
| ApoE4 allele | cleaved | cleaved |

Expressing the ApoE2, ApoE3, and ApoE4 alleles by 2, 3, and 4, respectively, the ApoE genetic polymorphism can take genotypes of 2/2, 2/3, 2/4, 3/3, 3/4, and 4/4. In the present invention, the ApoE genetic polymorphisms are classified into a genotype 4(+) having an allele 4 (that is, 2/4, 3/4 or 4/4) and a genotype 4(−) having no allele 4 (that is, 2/2, 2/3 or 3/3). And the ApoE genetic polymorphisms are classified into a genotype 3(+) having an allele 3/3 type (that is, 3/3) and a genotype 3(−) which includes all but 3/3 type (that is, 2/2, 2/3, 2/4, 3/4 and 4/4).

The method for measuring genetic polymorphisms of the present invention is not particularly limited so far as it can discern the polymorphism B(+) from polymorphism B(−) of the VDR gene, the polymorphism X(+) from polymorphism X(−) of the ER gene, and polymorphism 4(+) from polymorphism 4(−) of the ApoE gene, or polymorphism 3(+) from polymorphism 3(−) of the ApoE gene. Use may be made of various methods including appropriate combinations of genome DNA detection/analysis methods usually used, such as a southern hybridization method, a sequencing method, and a PCR method.

The methods for measuring these genetic polymorphisms are classified into three types based on their principle. That is, (1) a method in which a gene fragment containing the polymorphism site is isolated and the base sequence of the site is determined or the polymorphism site is directly detected by use of a specific probe or primer, (2) a method in which utilizing a difference in higher level structure of a gene fragment containing the polymorphism site, polymorphisms are distinguished based on electrophoretic mobility, and (3) a method in which utilizing the possibility of cleavage at the polymorphism site with a restriction enzyme, the polymorphisms are distinguished based on electrophoretic mobility. As specific examples of (1), mention may be made of, for example, a sequencing method, a sequence specific oligonucleotide probe (SSOP) method, amutant allele-specific amplification (MASA) method, etc.

In the sequencing method, firstly, specific primer pairs that can amplify respective gene fragments of appropriate lengths that contain respective polymorphism sites of the VRD gene, ER gene, and ApoE gene are synthesized. The primer pairs are not particularly limited so far as they have about 15 to about 40 bases and satisfy preferred conditions required for ordinary PCR primers. Then, using the pairs of primers, PCR is performed using a human-derived sample as a template to amplify the respective objective gene fragments. The reaction conditions for PCR may be selected suitably within the range usually used. The obtained amplified fragments may be subcloned in a suitable vector and the base sequence of each polymorphism site may be determined by a usual sequence using a Maxam-Gilbert method or a dideoxy method. Alternatively, the sequence may be determined directly without subcloning by a cycle sequencing method.

The SSOP method is a method that includes preparing a probe completely complementary to the sequence of one allele, performing southern hybridization of the genome DNA extracted from a human-derived sample with the probe while strictly controlling the hybridization temperature, and discriminating genetic polymorphisms by presence or absence of formation of hybrids. The hybridization may be carried out either separately for each gene or simultaneously provided that in order to prevent cross reactions with the probe, including mismatch, the hybridization conditions are controlled highly precisely since the polymorphisms of the three genes to be measured in the present invention are single base substitutions, respectively. It is desirable that the probe be designed such that the polymorphism site is present in the vicinity of the center of the probe in order to maximize stabilization due to mismatch. As a preferred variation, mention may be made of a PCR-SSOP method in which the fragment containing the polymorphism site is amplified by PCR prior to the hybridization.

The MASA method is a method which includes synthesizing an oligo DNA of about 15 to 45 bases containing a polymorphism site and being completely homologous (or completely complementary) to one allele sequence as one of the primers, carrying out PCR using a human-derived sample as a template while strictly controlling an annealing temperature, and discriminating genetic polymorphisms by the presence or absence of amplification products. In this method, like the above methods, the conditions of PCR for preventing cross-reactions must be highly precisely controlled. Conducting the reaction in an automatic thermal cycler enables one to make accurate discrimination relatively easily.

As the method (2) above, mention may be made of a PCR-SSCP (single-strand conformation polymorphism) method, a PCR-DGGE (denaturing gradient gel electrophoresis) method, a PCR-CFLP (cleavase fragment length polymorphism) method, etc. Each of these methods includes as the first step the amplification of respective gene fragments having suitable lengths containing a polymorphism site inside thereof in the same manner as in the sequencing method (1) above.

In the PCR-SSCP method, the amplification products are denatured into single strands by heating, treatment with an alkali, or the like. The DNA fragments dissociated into single strands form unique high level structures of their own depending on the base sequences so that the polymorphisms of one base substitution can be detected as a difference in mobility by electrophoresis on a non-denatured gel such as polyacrylamide gel.

In the PCR-DGGE method, after they are denatured/re-associated, the amplification products are electrophoresed on a denatured gel with a concentration gradient using a denaturant (SDS, urea, formamide, or the like). Since polymorphism of one base substitution changes the melting point (Tm) of the domain containing it, it partially dissociates at the position where the concentration of the denaturant differs and as a result it shows a different mobility. In particular, in the case of hetero conjugate DNA, wild type and mutant type homoduplexes and two types of heteroduplexes having mismatches are produced by denaturation and re-association. Therefore, four bands are detected. However, in the case where mutation is contained in the domain having the highest Tm, no difference occurs in mobility. In this case, with the addition of a GC-rich sequence of about 20 to about 50 bp, called GC clamp, to the 5'-side of the DNA, this portion becomes a domain having the highest Tm so that the polymorphism can be detected as a difference in mobility.

The PCR-CFLP method denatures the amplification product into single strands by heating or alkali treatment and then treats them with an enzyme called cleavase that recognizes and cleaves a hairpin structure and thereafter performs gel electrophoresis. It can detect the presence or absence of hairpin structure due to polymorphism or difference in hairpin forming site as a difference in the number of bands and/or in mobility.

The method (3) above is preferable since it can measure genetic polymorphism rapidly and easily. As such a method, mention may be made of an RFLP method, a PCR-RFLP method and the like.

The RFLP method is a method that includes digesting genome DNA isolated from a human-derived sample with a restriction enzyme that can cleave one of genetic polymorphisms at the polymorphism site (and optionally with another enzyme that can cleave the genome DNA at suitable sites upstream and downstream, respectively, of the polymorphism site), performing southern hybridization using a partial sequence or the whole sequence of the gene concerned as a probe, and discriminating polymorphisms based on the length and number of bands. In the present invention, Bsm I is used for the analysis of the VDR gene, Xba I is used for the analysis of the ER gene, and Hha I is used for the analysis of the ApoE gene.

The PCR-RFLP method is a method that includes synthesizing specific primer pairs that can amplify respective gene fragments of appropriate lengths containing inside thereof respective polymorphism sites of the VDR gene, ER gene and ApoE gene, performing PCR using the primer pairs and a human-derived sample as a template to amplify the objective respective gene fragments, performing treatment of the amplification products with a restriction enzyme similar to the above RFLP method, carrying out gel electrophoresis, and discriminating polymorphisms based on the length and number of bands. If the restriction enzyme treatment is performed prior to PCR, DNA cleaved with the restriction enzyme is not gene-amplified so that polymorphisms can be discriminated by the presence or absence of bands.

By the polymorphism analysis of the present invention as described above, human-derived samples are classified into [B(-) X(-) 4(-)], [B(-) X(-) 4(+)], [B(-) X(+) 4(-)], [B(-) X(+) 4(+)], [B(+) X(-) 4(-)], [B(+) X(-) 4(+)], [B(+) X(+) 4(-)], and [B(+) X(+) 4(+)] based on combinations of genetic polymorphisms of the VDR gene, ER gene, and ApoE gene. Otherwise, human-derived samples are classified into [B(-) X(-) 3(-)], [B(-) X(-) 3(+)], [B(-) X(+) 3(-)], [B(-) X(+) 3(+)], [B(+) X(-) 3(-)], [B(+) X(-) 3(+)], [B(+) X(+) 3(-)], and [B(+) X(+) 3(+)] based on combinations of genetic polymorphisms of the VDR gene, ER gene and ApoE gene.

The present invention is characterized by anticipating, based on a combination of the genetic polymorphisms, that the human-derived sample is derived from an individual who shows a specified priority of sensitivities to a plurality of remedies for osteoporosis. In the present invention, the pluralities of remedies for osteoporosis are preferably vitamin D, estrogen, and vitamin K2. Here, the sensitivity to a remedy for osteoporosis means the degree of therapeutic effect of the remedy on osteoporosis. That is, in the case where a medicine A is higher in therapeutic effect than a medicine B in a patient, "the sensitivity of the patient to the medicine A is higher than the sensitivity to the medicine B". In the present invention, using a change in bone mineral density before and after administration of a medicine as an index of sensitivity, it is defined that the greater the value of "index of change in bone mineral density"–"index of change in anticipated bone mineral density", the higher is the sensitivity to the medicine.

The analytical method of the present invention is characterized in that in the case where the combination of genetic polymorphisms of the vitamin D receptor gene, estrogen receptor gene, and apolipoprotein E gene is [B(-) X(-) 4(-)] and [B(+) X(-) 4(-)], it can be anticipated that the sample is derived from an individual who has a sensitivity to vitamin K2 that is higher than the sensitivity to vitamin D and the sensitivity to estrogen, in the case where the combination of genetic polymorphisms of the vitamin D receptor gene, estrogen receptor gene, and apolipoprotein E gene is [B(-) X(-) 4(+)], it can be anticipated that the sample is derived from an individual who has a sensitivity to vitamin D that is higher than the sensitivity to vitamin K2 and the sensitivity to estrogen, and in the case where the combination of genetic polymorphisms of the vitamin D receptor gene, estrogen receptor gene, and apolipoprotein E gene is [B(-) X(+) 4(-)], [B(-) X(+) 4(+)], [B(+) X(+) 4(-)] and [B(+)X(+)4(+)], it can be anticipated that the sample is derived from an individual who has a sensitivity to estrogen that is higher than the sensitivity to vitamin D and the sensitivity to vitamin K2.

In another embodiment, the present invention is characterized in that in the case where the combination of genetic polymorphism of the vitamin D receptor gene, estrogen receptor gene, and apolipoprotein E gene is [B(+) X(+) 3(+)] and [B(+) X(-) 3(+)], it can be anticipated that the sample is derived from an individual who has a sensitivity to vitamin K2 that is higher than a sensitivity to vitamin D and the sensitivity to estrogen, in the case where the combination of genetic polymorphism of the vitamin D receptor gene, estrogen receptor gene, and apolipoprotein E gene is [B(-) X(-) 3(+)], [B(-) X(-) 3(-)] or [B(+) X(-) 3(-)], it can be anticipated that the sample is derived from an individual who has a sensitivity to vitamin D that is higher than the sensitivity to vitamin K2 and the sensitivity to estrogen, and in the case where the combination of genetic polymorphism of the vitamin D receptor gene, estrogen receptor gene, and apolipoprotein E gene is [B(-) X(+) 3(+)], [B(-) X(+) 3(-)], or [B(+) X(+) 3(-)], it can be anticipated that the sample is derived from an individual who has a sensitivity to estrogen that is higher than the sensitivity to vitamin D and the sensitivity to vitamin K2.

Table 1

| | | |
|---|---|---|
| vitamin K2 > vitamin D or estrogen | [B(−)X(−)4(−)]<br>[B(+)X(−)4(−)] | [B(+)X(+)3(+)]<br>[B(+)X(−)3(+)] |
| vitamin D > vitamin K2 or estrogen | [B(−)X(−)4(+)] | [B(−)X(−)3(+)]<br>[B(−)X(−)3(−)]<br>[B(+)X(−)3(−)] |
| estrogen > vitamin K2 or vitamin D | [B(−)X(+)4(−)]<br>[B(−)X(+)4(+)]<br>[B(+)X(+)4(−)]<br>[B(+)X(+)4(+)] | [B(−)X(+)3(+)]<br>[B(−)X(+)3(−)]<br>[B(+)X(+)3(−)] |

[B(+)X(−)4(+)] is deemed not to be sensitive for any one of the three agents.

The present invention also provides a kit for analyzing the genetic polymorphism of a sample containing human genome DNA useful for practicing the above analytical method. The kit of the present invention comprises a pair of primers that can specifically amplify a vitamin D receptor gene, a pair of primers that can specifically amplify an estrogen receptor gene, a pair of primers that can specifically amplify an apolipoprotein E gene, and/or nucleic acid probes that can specifically hybridize with the vitamin D receptor gene, nucleic acid probes that can specifically hybridize with the estrogen receptor gene, and nucleic acid probes that can specifically hybridize with the apolipoprotein E gene.

In the case where a PCR-SSOP method, a PCR-SSCP method, a PCR-DGGE method, a PCR-CFLP method, etc. are used in the analysis of polymorphisms, the respective primer pairs used are oligonucleotides having the same base sequences as the sequence upstream of the polymorphism site of each gene and the sequence downstream of the polymorphism site of each gene and a sequence so that the respective gene fragments containing the polymorphism sites inside thereof can be amplified. On the other hand, in the case where the MASA method is used, one of the primers is one having a base sequence that is completely homologous (=sense) or completely complementary (=antisense) to the region containing the polymorphism site of each gene.

In the case where the RFLP method is used in the analysis of polymorphisms, the nucleic acid probe is not particularly limited in so far as it contains a part of the sequence of each gene. On the other hand, in the case where the SSOP method or the PCR-SSOP method is used in the analysis of polymorphisms, the nucleic acid probe is one having a base sequence that is completely complementary to the sequence of the region containing the polymorphism site of each gene.

The primer specific to the VDR gene used in the present invention is, among those oligonucleotides designed so as to amplify by polymerase chain reaction (hereinafter, PCR) the VDR gene region containing the Bsm I restriction enzyme polymorphism of intron 8 of VDR as the detection target site of the present invention by PcR, one having Tm that is close to those of amplification primers of the ApoE gene and ER gene. Specifically, the following amplification primers can be exemplified as ones having an annealing temperature upon PCR being 50° C.

```
gtgcaggcga ttcggtaggg    20    (SEQ ID NO: 1) and ccagcggaag aggtcaaggg    20    (SEQ ID NO: 2)
```

The primer specific to the ApoE gene used in the present invention is, among those oligonucleotides designed so as to amplify the ApoE gene region containing ApoE polymorphism as the detection target site of the present invention by PCR, one having Tm that is close to those of amplification primers of VDR gene and ER gene. Specifically, the following pairs of amplification primers can be exemplified as one having an annealing temperature upon PCR being 50° C.

```
ctgggcgcgg acatgg        16    (SEQ ID NO: 3) and cccggcctgg tacact        16    (SEQ ID NO: 4), or ctgggcgcgg acatggagga    20    (SEQ ID NO: 5) and cccggcctgg tacactgcca    20    (SEQ ID NO: 6),
```

The primer specific to the ER gene used in the present invention is, among those oligonucleotides designed so as to amplify the ER gene region containing the Xba I restriction enzyme polymorphism of intron 1 of ER as the detection target site of the present invention by PCR, one having Tm that is close to those of amplification primers of VDR gene and ApoE gene. Specifically, the following pair of amplification primers can be exemplified as one having an annealing temperature upon PCR being 50° C.

```
gttccaaatg tcccagccgt    20    (SEQ ID NO: 7) and cctgcaccag aatatgtacc    20    (SEQ ID NO: 8), or gttccaaatg tcccagccgt    20    (SEQ ID NO: 7) and cctgcaccag aatatgttac c  21    (SEQ ID NO: 9)
```

The probe for detecting the VDR gene used in the present invention is, among those oligonucleotides bound to the type B or type b at the Bsm I polymorphism site of the VDR gene, one having Tm close to those of the detection probes for the ApoE gene and ER gene. Specifically, in the case where the temperature upon hybridization is 45° C., the following detection probes can be exemplified.

```
caggcctgcg cattcc        16    (SEQ ID NO: 10)

caggcctgca cattcc        16    (SEQ ID NO: 11)
```

The probe for detecting the ApoE gene used in the present invention is, among those oligonucleotides bound to the type 4(+) or type 4(−) at the polymorphism site of the ApoE gene, one having Tm close to those of the detection probes for the VDR gene and ER gene. Specifically, in the case where the temperature upon hybridization is 45° C., the following pair of detection probes can be exemplified.

```
aggacgtgcg cggc          14    (SEQ ID NO: 12) and aggacgtgtg cggcc         15    (SEQ ID NO: 13)
```

In order to classify the ApoE gene into 2/2, 2/3, 2/4, 3/3, 3/4 or 4/4 allele, the following four probes can be used,

```
aggacgtgcg cggc          14    (SEQ ID NO: 12)

aggacgtgtg cggcc         15    (SEQ ID NO: 13)

cagaagcgcc tggcag        16    (SEQ ID NO: 18) and cagaagtgcc tggcag        16    (SEQ ID NO: 19)
```

The probe for detecting the ER gene used in the present invention is, among those oligonucleotides bound to the type X or type x at the Xba I polymorphism site of the ER gene, one having Tm close to those of the detection probes for VDR gene and ApoE gene. Specifically, in the case where the temperature upon hybridization is 45° C., the following pair of detection probes can be exemplified.

```
gtgtggtcta gagttg    16   (SEQ ID NO: 14) and gtgtggtctg gagttg    16   (SEQ ID NO: 15), or tctggagttg ggatga    16   (SEQ ID NO: 16) and gtggtctaga gttggg    16   (SEQ ID NO: 17)
```

The reagent for amplifying the VDR, ApoE and ER genes of the present invention includes the above amplification primers (1), (2), (3), (4), (7) and (8), or (1), (2), (5), (6), (7) and (8), or (1), (2), (3), (4), (7) and (9) or (1), (2), (5), (6), (7) and (9).

The amplification reagent further comprises heat-resistant DNA polymerases, dNTPs and buffers. As the heat resistant DNA polymerases, Taq DNA polymerase, Tth DNA polymerase, Pfu DNA polymerase, etc. can be exemplified. The dNTPs means a mixture of dATP, dCTP, dGTP and dTTP. Further, the buffer may be selected depending on the heat resistant DNA polymerase used. For example, Tris buffer solutions containing Mg ions, glycerol, etc. are used for Taq polymerase.

The reagent for simultaneously detecting genetic polymorphisms of the VDR, ApoE4 types and ER genes of the present invention includes the above detection probes (10), (11), (12), (13), (14) and (15), or (10), (11), (12), (13), (16) and (17), or (10), (11), (12), (13), (18), (19), (14) and (15), or (10), (11), (12), (13), (18), (19), (16) and (17).

The amplification primers or detection probes may be bound to a labeled substance directly or indirectly. As the labeled substances, radioactive substances, enzymes, fluorescent substances or biotin can be exemplified.

When the labeled substance is a radioactive substance, its dose is measured. When the labeled substance is an enzyme, for example, alkaline phosphatase, 5-bromo-4-chloro-3-indole phosphoric acid p-toluidine salt (BCIP) and nitro blue tetrazolium (NBT) are acted thereon and the intensity of color development of the product is measured. A luminescent substance such as 1,2-dioxetane compound may be acted on alkaline phosphatase and the amount of luminescence generated upon decomposition of the compound may be measured. Enzymes other than alkaline phosphatase, such as peroxidase, may also be used by conventional methods. If the labeled substance is biotin, for example, alkaline phosphatase-bound avidin is reacted after PCR and the alkaline phosphatase after the reaction is measured by a conventional method.

The reagent for simultaneously detecting the genetic polymorphisms of the VDR, ApoE4 types and ER genes of the present invention may further contain the above amplification primers (1), (2), (3), (4), (7), and (8), or (1), (2), (5), (6), (7) and (8), or (1), (2), (3), (4), (7) and (9), or (1), (2), (5), (6), (7) and (9); and the above detection probes (10), (11), (12), (13), (14) and (15), or (10), (11), (12), (13), (16) and (17), or (10), (11), (12), (13), (18), (19), (14) and (15), or (10), (11), (12), (13), (18), (19), (16) and (17).

In the above amplification reagent, the primer is at 0.1 to 1.0 μM in the PCR final composition. Further, it is preferred that the probe is at 0.1 to 1.0 pmol/μL in the above detection reagents.

In the present invention, the organism samples used in the method for detecting the above genetic polymorphisms are not particularly limited so far as they are genomes collected from organisms producing the above proteins (VDR, ApoE, and ER). For example, there are genomes (DNAs) extracted from human blood cell components with phenol or the like and optionally purified.

The method for detecting the genetic polymorphisms of the VDR, ApoE and ER genes of the present invention is consistent with common methods for detecting genes. That is, it is a method in which the DNA in a sample is amplified with an amplification reagent containing an amplification primer specific to the VDR, ApoE and ER genes, then the genetic polymorphisms of the VDR, ApoE and ER genes in the sample are detected using a detection reagent containing detection probes for detecting the genetic polymorphism of the VDR, ApoE and ER genes.

Specifically, it is a method in which the DNA in the sample, for example, DNA purified from human blood, is amplified using an amplification reagent containing the above amplification primers, and the genetic polymorphisms of the VDR, ApoE and ER genes in the sample are detected from the amplified sample using the above detection probes.

One of the amplification methods is a method generally referred to as a polymerase chain reaction (hereinafter, PCR) method, in which double-strand sample DNA is heated to convert it into single strands, an amplification primer is annealed using the single strands as templates, and then the temperature is elevated to synthesize dNTPs from the primers by means of DNA polymerases and extend their length. The obtained double-strand is dissociated into single strands, and repetition of the above reactions can efficiently amplify DNA having the target region. Generally, the reaction conditions are 92 to 95° C. for 30 seconds to 1 minute, 50 to 65° C. for 20 seconds to 1 minute, 70 to 75° C. for 20 seconds to 5 minutes, this cycle being repeated 20 to 40 times. In the region of 50 to 65° C., the above annealing occurs. The annealing temperature at which the reaction will proceed successfully is regulated mainly by the composition of the primer. In the region of 70 to 75° C., extension occurs and the length of the target region to be amplified regulates the time for which the reaction will proceed successfully.

The detection method means a method in which the DNA amplified by the above amplification method is detected by means of a detection probe. It is preferred that the amplification primer be bound to a labeled substance. Plural labeled substances may be bound to the primer.

In the present invention, for example, immobilizing three kinds of detection probes to one solid phase carrier and binding amplified sample DNA to the probe makes it possible to detect the genetic polymorphisms of the VDR, ApoE and ER genes on the solid phase carrier. As the solid phase carrier, nylon membrane, microtiter plate, etc. can be used. To immobilize the detection probes to the solid phase carrier, for example, a method is used in which dTTP is linearly added to the terminal of the detection probe by terminal deoxynucleotidyl transferase (TdT) (polyT addition) and physically adsorbed to the above carrier. Three genetic polymorphisms in one amplified sample can be simultaneously judged by providing the detection probes for the VDR, ApoE and ER genes in a solid phase or immobilizing them to, for example, separate sites on a nylon membrane or individual wells of a microtiter plate.

The amplified DNA hybridized with the detection probe on the solid phase carrier can be detected by measuring the labeled substance that binds thereto. For example, as shown in FIG. 1, the sample that reacts with the detection prode (10) is judged to be of the type VDR B(+), that means BB or Bb. The sample that does not react with the detection prode (10) is judged to be of the type VDR B(−), that is bb. The detection prode (11) is a control to identify the amplification of the VDR gene. The sample that reacts with the detection prode (12) is judged to be of the type ApoE4(+). But the sample that does not react with the detection prode (12) is judged to be of the type ApoE4(−). The detection prode (13) is a control to identify the amplification of the ApoE gene. The sample that reacts with the detection prode (14) is judged to be of the type ER X(+). The sample that does not react with the detection prode (14) is judged to be of the type ER X(−). The detection probe (15) is a control to identify the amplification of the ER gene. From these combinations, the genetic polymorphisms of the three genes in the sample can be detected.

The kit of the present invention may further contain various reagents and/or apparatus suitable for practicing the analytical method of the present invention.

The method for selecting a bone-associated remedy of the present invention can relate the combinations of genetic polymorphisms of the VDR, ApoE and ER genes detected by the method for detecting genetic polymorphisms of the VDR, ApoE and ER genes described above to remedies for bone-associated diseases. That is, the human sample whose VDR genetic polymorphism is of the type B(−) is judged to have a high sensitivity to vitamin D. The human sample whose VDR genetic polymorphism is of the type B(+) and whose ApoE genetic polymorphism is of the typE4(−) is judged to have a high sensitivity to vitamin K2. The human sample whose VDR genetic polymorphism is of the type B(+), whose ApoE genetic polymorphism is of the typE4(+), and whose ER genetic polymorphism is of the type X(+) is judged to have a high sensitivity to estrogen. Further, the human sample whose VDR genetic polymorphism is of the type B(+), whose ApoE genetic polymorphism is of the typE4(+), and whose ER genetic polymorphism is of the type(−) is judged to have low sensitivities to vitamin D, vitamin K2, and estrogen so that it is possible to study administration of a medicine other than the three medicines.

In the present invention, the following probes can be used for detecting ApoE 3 type polymorphism instead of the detection probes above mentioned.

Detection probes for detecting the polymorphism of ApoE gene:

```
aggacgtgcg cggc      14    (SEQ ID NO: 12)

aggacgtgtg cggcc     15    (SEQ ID NO: 13)

cagaagcgcc tggcag    16    (SEQ ID NO: 18)

cagaagtgcc tggcag    16    (SEQ ID NO: 19)
```

ApoE 2 type polymorphism can be reacted with detection probes (13) and (19), ApoE3 type polymorphism with detection prodes (13) and (18), and ApoE4 type polymorphism with detection prodes (12) and (18). The polymorphism which reacts with the detection probes (12), (13) and (18) but not (19) is ApoE3/4 type. The polymorphism that can only react with detection prodes (13) and (18) is 3(+) type (=3/3 type) and other polymorphism is 3(−) type.

The detection kit of this invention may also comprise suitable agents and/or apparatus in order to practice the present detection method.

EXAMPLES

Hereinafter, the present invention will be explained in detail by reference examples and examples.

REFERENCE EXAMPLE 1

Blood was collected from 177 Japanese females after menopause randomly selected and blood cells were frac-tionated and genome DNA was extracted and purified by conventional methods. A VDR gene fragment, an ER gene fragment, and an ApoE gene fragment were separately amplified using the genome DNA as a template and the following primer pairs.

Primers for amplifying the VDR gene fragment:

Sense:
5'-CAACCAAGACTACAAGTACCGCGTCAGTGA-3'(SEQ ID NO: 20)

Antisense: 5'-AACCAGCGGGAAGAGGTCAAGGG-3' (SEQ ID NO: 21)

Primers for amplifying the ER gene fragment:

Sense: 5'-CTGCCACCCTATCTGTATCTTTTCCTATT CTCC-3'(SEQ ID NO: 22)

Antisense:
5'-TCTTTCTCTGCCACCCTGGCGTCGATTAT CTGA-3'(SEQ ID NO: 23)

Primers for amplifying the ApoE gene fragment:

Sense: 5'-CGGGCACGGCTGTCCAAGGAG-3'(SEQ ID NO: 24)

Antisense: 5'-CACGCGGCCCTGTTCCACGAG-3'(SEQ ID NO: 25)

The PCR conditions were denaturation: 94° C., 60 seconds; annealing: 62° C., 60 seconds; elongation: 72° C., 60 seconds (30 cycles) for the VDR gene, denaturation: 94° C., 30 seconds; annealing: 65° C., 30 seconds; elongation: 72° C., 30 seconds (30 cycles) for the ER gene, and denaturation: 94° C., 30 seconds; annealing: 61° C., 40 seconds; elongation: 72° C., 90 seconds (30 cycles) for the ApoE gene. This PCP amplification gave a VDR gene fragment of 7.2 kbp, an ER gene fragment of 1.3 kbp, and an ApoE gene fragment of 244 bp containing polymorphism sites, respectively. After treating a VDR gene amplification reaction mixture with Bsm I, an ER gene amplification reaction mixture with Xba I, and an ApoE gene amplification reaction mixture with Hha I, the reaction mixtures were subjected to agarose gel electrophoresis. In the case where each amplification product was cleaved with the restriction enzyme at the polymorphism site, bands of 4.6 kbp and 2.6 kbp were detected for the VDR amplification product, bands of 900 bp and 400 bp were detected for the ER amplification product, and bands of 72,48, 38, 35, 19, 17, and 15 bp were detected for the ApoE amplification product.

The band of 72 bp was not detected in the case where there is no typE4 (that is, 4(−)). After the electrophoresis, the gels were dyed with ethidium bromide and polymorphisms of the VDR, ER, and ApoE genes were discriminated based on the band patterns and classified into 8 polymorphism groups (Table 3).

The 177 Japanese females after the polymorphism analysis as described above were each measured for bone mineral density. Then, one of vitamin D, estrogen, and vitamin K2 was administered to the patients for 6 months. The administration amount was 1μg/day for vitamin D, 0.312 mg/day for estrogen, and 45 mg/day for vitamin K2. After 6 months, the bone mineral density was measured again and an index of change in bone mineral density between before and after the administration of a medicine was obtained. A value obtained by subtracting an anticipated value of therapeutic effect of each medicine (total average therapeutic effect on randomly sampled patients; Table 3) from an average index of change in bone mineral density for each genotype was defined as sensitivity to a medicine for each genotype. The results are shown in Table 3.

TABLE 2

Anticipated therapeutic effect value (index of change in bone mineral density) after 6 month administration of a medicine (unit: %)

|  | Vitamin D | Estrogen | Vitamin K2 |
|---|---|---|---|
| N | 104 | 38 | 27 |
| Average | 1.15 | 3.26 | 0.59 |

N: number of samples

TABLE 3

Average therapeutic effect (%) - Anticipated therapeutic effect (%) for each genotype

| Genotype | | Vitamin D | Estrogen | Vitamin K2 |
|---|---|---|---|---|
| B(−)X(−)4(−) | n | 42 | 22 | 11 |
|  | Average | 0.05 | −0.94 | 0.68 |
| B(−)X(−)4(+) | n | 14 | 4 | 6 |
|  | Average | 0.56 | −2.52 | −2.68 |
| B(−)X(+)4(−) | n | 16 | 7 | 5 |
|  | Average | 0.37 | 2.78 | 0.60 |
| B(−)X(+)4(+) | n | 8 | 2 | |
|  | Average | 0.34 | 7.87 | |
| B(+)x(−)4(−) | n | 14 | 5 | 3 |
|  | Average | −0.66 | −0.93 | 1.08 |
| B(+)x(−)4(+) | n | 4 | 3 | 1 |
|  | Average | −0.27 | −1.07 | −0.59 |
| B(+)x(+)4(−) | n | 5 | 2 | 2 |
|  | Average | −1.75 | 1.74 | 1.46 |
| B(+)x(+)4(+) | n | 1 | 0 | 0 |
|  | Average | 0.46 | | | n: number of samples

As will be apparent from Table 3, in the case where the genotypes included [B(−) X(−) 4(−)] and [B(+) X(−) 4(−)], the sensitivity to vitamin K2 was higher than the sensitivity to vitamin D and the sensitivity to estrogen. In the case where the genotype included [B(−) X(−) 4(−)], the sensitivity to vitamin D was higher than the sensitivity to vitamin K2 and the sensitivity to estrogen. In the case where the genotypes included [B(−) X(+) 4(−)], [B(−) X(+) 4(+)], [B(+) X(+) 4(−)] and [B(+) X(+) 4(+)], the sensitivity to estrogen was higher than the sensitivity to vitamin D and the sensitivity to vitamin K2.

Example 1

Blood is collected from a Japanese patient suffering from osteoporosis and blood cells are fractionated and DNA is extracted and purified by conventional methods. The polymorphisms of the VDR gene, ER gene, and ApoE gene are analyzed in the same manner as in Reference Example 1. In the case where the genotype included [B(−) X(−) 4(−)] and [B(+) X(−) 4(−)], it can be anticipated that the genome DNA is derived from an individual who has a sensitivity to vitamin K2 that is higher than the sensitivity to vitamin D and the sensitivity to estrogen, and in the case where the genotype included [B(−) X(−) 4(+)], it can be anticipated that the genome DNA is derived from an individual who has a sensitivity to vitamin D that is higher than the sensitivity to vitamin K2 and the sensitivity to estrogen. Further, in the case where the genotype included [B(−) X(+) 4(−)], [B(−) X(+) 4(+)], [B(+) X(+) 4(−)], and [B(+) X(+) 4(+)] it can be anticipated that the genome DNA is derived from an individual who has a sensitivity to estrogen that is higher than the sensitivity to vitamin D and the sensitivity to vitamin K2.

Reference Example 2

Blood was collected from 167 Japanese females after menopause randomly selected and blood cells were fractionated and genome DNA was extracted and purified by conventional methods. A VDR gene fragment, an ER gene fragment and an ApoE gene fragment were separately amplified using the genome DNA as a template and the same primer pairs as in Reference Example 1 under the same amplification conditions.

After treating the gene amplification reaction mixtures with a restriction enzyme respectively, the reaction mixtures were subjected to agarose gel electrophoresis. In the case where each amplification product was cleaved with the restriction enzyme at the polymorphism site, bands of 4.6 kbp and 2.6 kbp were detected for the VDR amplification product, bands of 900 bp and 400 bp were detected for the ER amplification product, and bands of 72, 48, 38, 35, 19, 17, and 15 bp were detected for the ApoE amplification product.

To detect ApoE3 type alleles, the amplification products were treated with Hha I, and were subjected to agarose electrophoresis gel. After the electrophoresis, the gels were dyed with ethidium bromide and polymorphisms of the ApoE genes were discriminated based on the band patterns and ApoE3 types identified as a combination of bands as below described.

2/2 type: 16, 18, 38, 81, 91bp
2/3 type: 16, 18, 33, 38, 48 , 81, 91bp
2/4 type: 16, 18, 19, 33, 38, 48, 72, 81, 91bp
3/3 type: 16, 18, 33, 38, 48, 91bp
3/4 type: 16, 18, 19, 33, 38, 48, 72, 91bp
4/4 type: 16, 18, 19, 33, 38, 48, 72bp The 8 polymorphism groups were classified (Table 4).

TABLE 4

Average therapeutic effect (%) - Anticipated therapeutic effect (%) for each genotype

| Genotype | | Vitamin D | Estrogen | Vitamin K2 |
|---|---|---|---|---|
| B(+)X(+)3(+) | n | 6 | 3 | 1 |
|  | Average | −0.69271 | 0.414441 | 3.247953 |
| B(+)X(−)3(+) | n | 14 | 6 | 2 |
|  | Average | 0.020422 | −0.89605 | 1.85249 |
| B(−)X(+)3(+) | n | 13 | 6 | 6 |
|  | Average | 1.643171 | 3.74052 | −0.20826 |
| B(−)X(−)3(+) | n | 36 | 14 | 10 |
|  | Average | 0.401685 | −0.07099 | −0.84426 |
| B(+)X(+)3(−) | n | 1 | 0 | 0 |
|  | Average | 0.461047 | | |
| B(+)X(−)3(−) | n | 4 | 3 | 0 |
|  | Average | 2.234264 | 0.03227 | |
| B(−)X(+)3(−) | n | 10 | 1 | 0 |
|  | Average | −3.11426 | 4.513852 | |
| B(−)X(−)3(−) | n | 16 | 10 | 5 |
|  | Average | 1.498286 | −1.15117 | −2.85484 | n: number of samples

From Table 4, it can be anticipated that the sample is derived from an individual who has a sensitivity to vitamin K2 that is higher than the sensitivity to vitamin D and the sensitivity to estrogen in the case where the combination of genetic polymorphisms of the vitamin D receptor gene, estrogen receptor gene, and apolipoprotein E gene includes [B(+) X(−) 3(+)] and [B(+) X(+) 3(+)]. And it can be anticipated that the sample is derived from an individual who has a sensitivity to vitamin D that is higher than the sensitivity to vitamin K2 and the sensitivity to estrogen in the case where the combination includes [B(−) X(−) 3(+)], [B(−) X(−) 3(−)] and [B(+) X(+) 4(+)]. Further, it can be anticipated that the sample is derived from an individual who has a sensitivity to estrogen that is higher than the sensitivity to vitamin D and the sensitivity to vitamin K2 in the case where the combination includes [B(−) X(+) 3(+)], [B (−) X(+) 3(−)], and [B(+) X(+) 3(−)]

Example 2

Blood is collected from a Japanese patient suffering from osteoporosis and blood cells are fractionated and DNA is extracted and purified by conventional methods. The polymorphisms of the VDR gene, ER gene and ApoE gene are analyzed in the same manner as in Reference Example 2. In the case where the genotype included [B(+) X(+) 3(+)] and [B(+) X(−) 3(+)], it can be anticipated that the genome DNA is derived from an individual who has a sensitivity to vitamin K2 that is higher than the sensitivity to vitamin D and the sensitivity to estrogen, and in the case where the genotype included [B(−) X(−) 3(+)], [B(−) X(−) 3(−)] and [B(+)X(−) 3(−)], it can be anticipated that the genome DNA is derived from an individual who has a sensitivity to vitamin D that is higher than the sensitivity to vitamin K2 and the sensitivity to estrogen. Further, in the case where the genotype included [B(−) X(+) 3(+)], [B(−) X(−) 3(−)], and [B(+) X(+) 3(−)], it can be anticipated that the genome DNA is derived from an individual who has a sensitivity to estrogen that is higher than the sensitivity to vitamin D and the sensitivity to vitamin K2.

Example 3

The following four kinds of reagents (1) to (4) were prepared.

| Reagent (1) | 50% | Glycerol |
| Reagent (2) | 5 mM | Magnesium chloride |
| Reagent (3) | 0.25 M | Sodium chloride |
| | 0.05 M | Tris-hydrochloric acid buffer |
| | 0.05% | Gelatin |
| | 1 mM | dNTPs |
| Reagent (4) | 3 μM | VDR primer (SEQ ID NO: 1), having a biotin combined to the 5′-terminal |
| | 3 μM | VDR primer (SEQ ID NO: 2) |
| | 3 μM | ApoE primer (SEQ ID NO: 3), having a biotin combined to the 5′-terminal |
| | 3 μM | ApoE primer (SEQ ID NO: 4) |
| | 3 μM | ER primer (SEQ ID NO: 7), having a biotin combined to the 5′-terminal |
| | 3 μM | ER primer (SEQ ID NO: 8) |

To 5 μl (n=8) DNA purified from human blood were added 10 μL each of the reagents (1) to (4) and further 4.8 μL of sterilized, purified water and 0.2 μL of heat-resistant DNA polymerase (ToYoBo Taq Polymerase) were added. The obtained solution was subjected to heating at 95° C. for 5 minutes [95° C. for 30 seconds, 50° C. for 20 seconds, or 72° C. for 20 seconds], the cycle being repeated 30 times and PCR was carried out under the condition of 72° C. for 10 minutes. The amplified product was subjected to agarose gel electrophoresis. The results are shown in FIG. 2.

Figure 2:
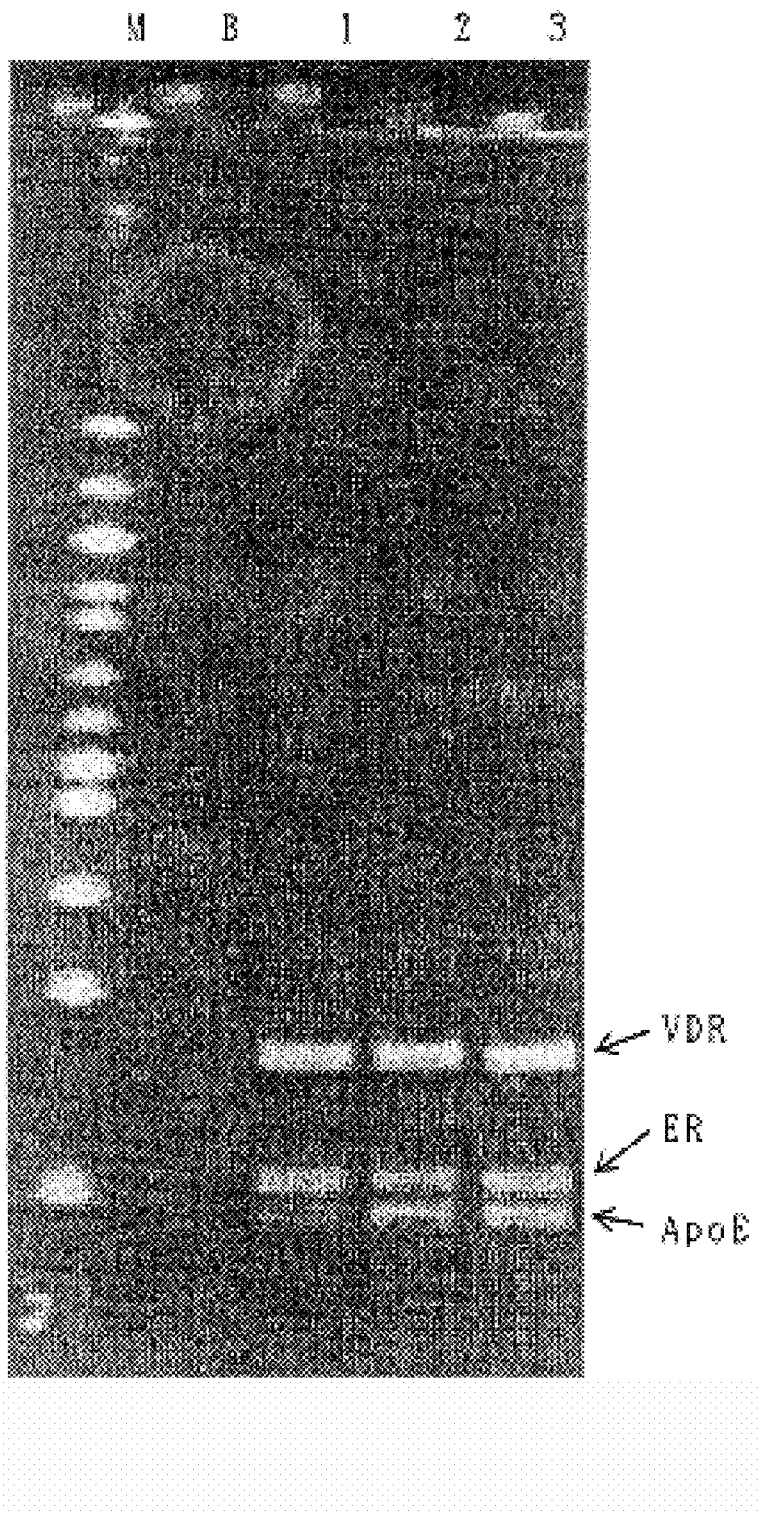
FIG. 2 is an electrophoretogram in lieu of a drawing, illustrating the results of electrophoresis of the genes amplified with the primers of the present invention.

As will be apparent from FIG. 2, bands attributable to the VDR, ApoE and ER genes were detected from each of the three samples.

Example 4

Instead of the ApoE primers having oligonucleotides SEQ ID NO: 3 and SEQ ID NO: 4 of Example 3, new primers having oligonucleotides SEQ ID NO: 5 and SEQ ID NO: 6, and instead of the ER primers having oligonucletides SEQ ID NO: 7 and SEQ ID NO: 8 of Example 3, new primers having oligonucleotides SEQ ID NO: 8 and SEQ ID NO: 9 were used to amplify the purified DNA from human blood in the same manner as Example 3. The amplified product was subjected to agarose gel electrophoresis. The results are similar to those in Example 3.

Example 5

PolyT addition was carried out to six probes, i.e., the VDR probes (SEQ ID NO: 10) and (SEQ ID NO: 11), the ApoE probes (SEQ ID NO: 12) and (SEQ ID NO: 13), and the ER probes (SEQ ID NO: 14) and (SEQ ID NO: 15) using TaKaRa terminal deoxynucleotidyl transferase and dTTP. The polyT-added probes were coated at separate sites on a single sheet of nylon membrane (4×0.4 cm) each in an amount of 0.5 μL. Ultraviolet ray at 312 nm was irradiated thereon for 2 minutes to immobilize them to prepare a detection strip.

Then, the following two kinds of reagents were prepared.

| Reagent (5) | 5 M | Sodium hydroxide |
| | 0.05 M | EDTA |
| Reagent (6) | 0.01% | SDS |
| | 1.8% | Sodium chloride |
| | 1% | Sodium citrate |

Figure 3:
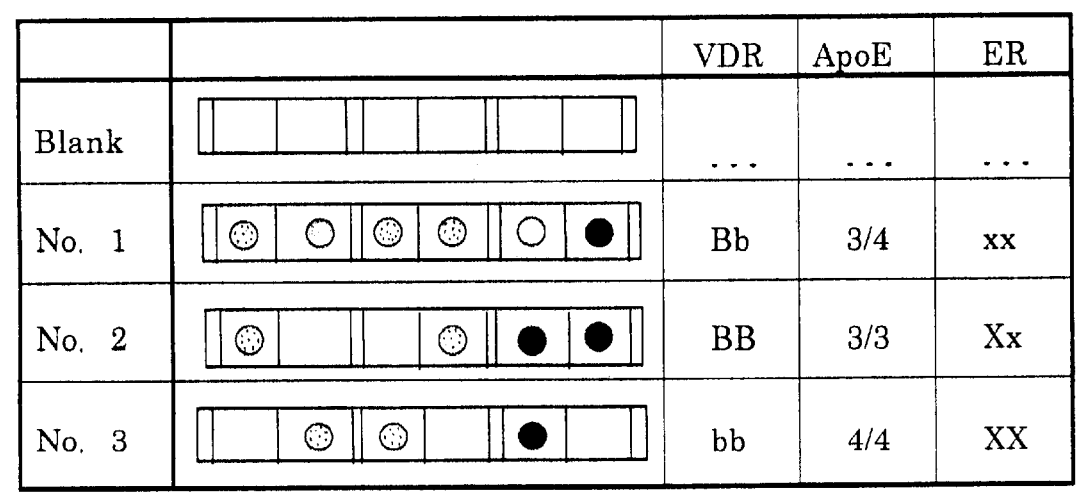

To 10 μL of the sample amplified in Example 3.was added 10 μL of the reagent (5) and the mixture was stirred well and then left to stand for 5 minutes. To the sample solution were added 1 mL of the reagent (6) and a piece of the above detection strip, followed by shaking at a reaction temperature of 45° C. for 30 minutes to cause the reaction to proceed. Thereafter, alkaline phosphatase bound to streptoavidin was added thereto. Further, BCIP and NBT were added thereto. These cause the alkaline phosphatase bound to the samples bound to the respective probes on the detection strip to develop colors. The results obtained from the intensities of color development are shown in FIG. 3.

From FIG. 3, the samples Nos. 1 to 8 were judged to have the genetic polymorphisms as shown in Table 5 below.

TABLE 5

| | VDR Genetic Polymorphism | ApoE Genetic Polymorphism | ER Genetic Polymorphism |
| --- | --- | --- | --- |
| Sample No. 1 | Bb | 4(+) | xx |
| Sample No. 2 | BB | 4(−) | Xx |
| Sample No. 3 | bb | 4(+) | XX |

Figure 4:
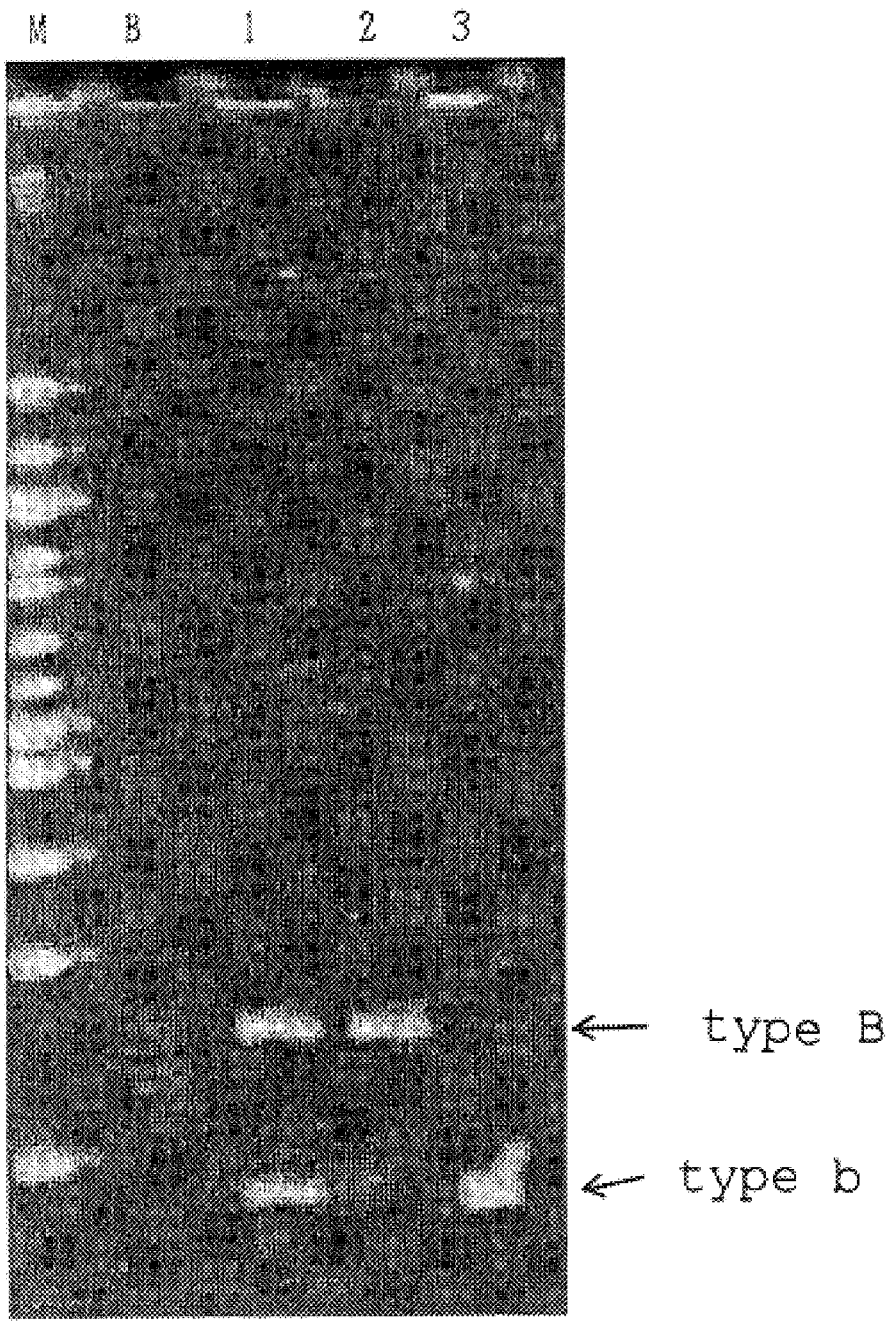
FIG. 4 is an electrophoretogram in lieu of a drawing, illustrating the results of electrophoresis on the samples of Example 5, obtained by amplifying only the VDR gene by a PCR method and discriminating the genetic polymorphism of VDR gene according to restriction enzyme fragment length with respect to restriction enzyme Bsm I.
Figure 5:
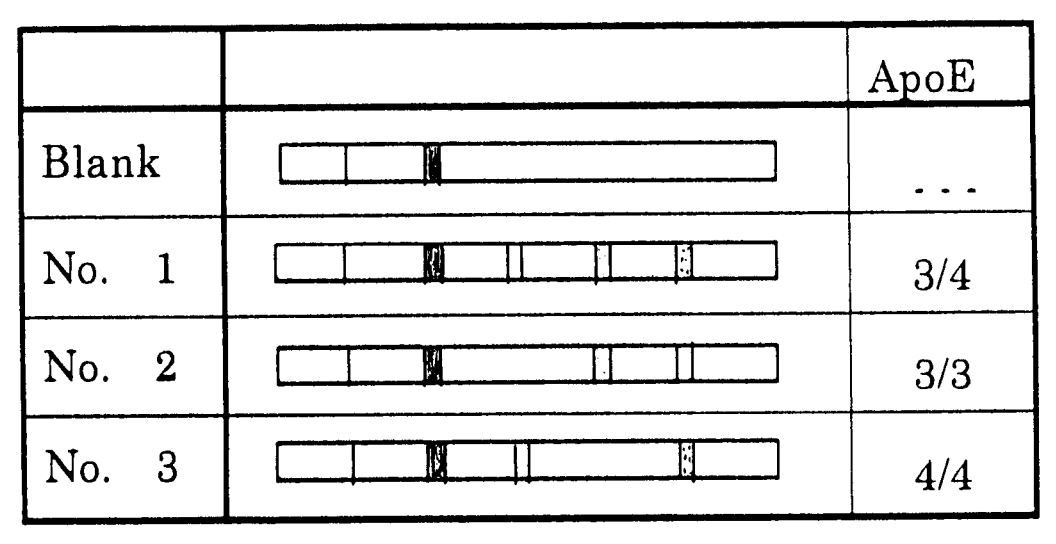
Figure 6:
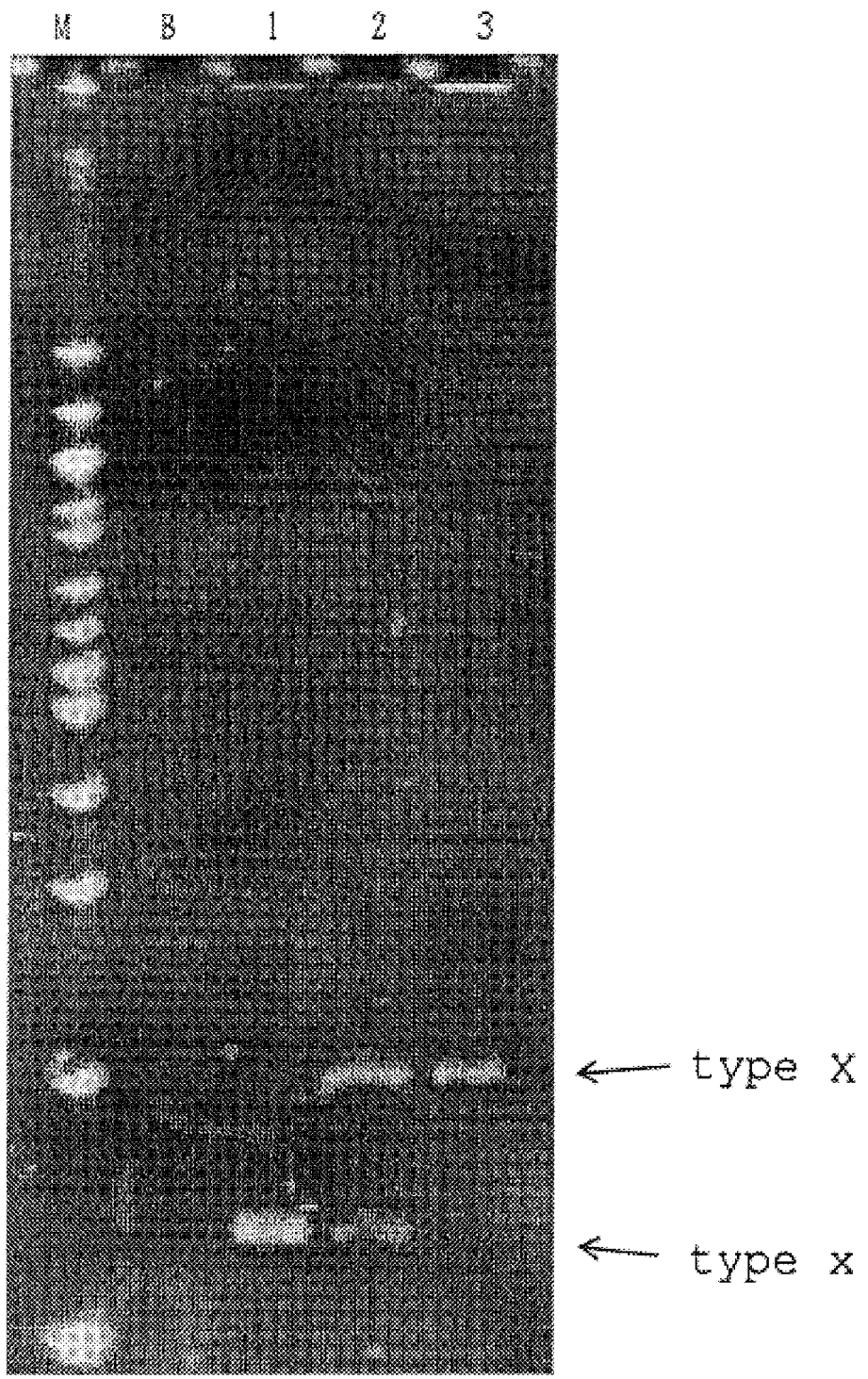
FIG. 6 is an electrophoretogram in lieu of a drawing, illustrating the results of electrophoresis on the samples of Example 6, obtained by amplifying only the ER gene by a PCR method and discriminating the genetic polymorphism of ER gene according to restriction enzyme fragment length with respect to restriction enzyme Xba I.

Of the samples used in Example 4, separately the genetic polymorphisms were judged based on the restriction enzyme fragment length by the restriction enzyme Bsm I for the VDR gene. For the ApoE gene, judgment was made using a reagent that detects only the genotype of ApoE (trade name: INNO-LiPA ApoE, manufactured by Innogenetics Corp.). Further, for the ER gene, judgment was made based on the restriction enzyme fragment length by the restriction enzyme Xba I. The results are shown in FIGS. 4 to 6 and Table 6.

TABLE 6

|  | VDR Genetic Polymorphism | ApoE Genetic Polymorphism | ER Genetic Polymorphism |
|---|---|---|---|
| Sample No. 1 | Bb | 3/4 | xx |
| Sample No. 2 | BB | 3/3 | Xx |
| Sample No. 3 | bb | 4/4 | XX |

As will be apparent from Tables 5 and 6, the results coincided with each other.

Using the detection reagent of the present invention, the three genes, i.e., VDR, ApoE and ER genes can be amplified simultaneously and the three genetic polymorphisms can be detected by a single operation using the amplified products. Further, since the genes are associated with osteoporosis, effective remedies for osteoporosis can be selected by use of the detection reagents based on a combination of genetic polymorphisms of the genes due to the results of detection of genetic polymorphisms.

Example 6

PolyT addition was carried out to eight probes, i.e., the VDR probes (SEQ ID NO: 10) and (SEQ ID NO: 11), the ApoE probes (SEQ ID NO: 12) and (SEQ ID NO: 13), (SEQ ID NO: 18) and (SEQ ID NO: 19), and the ER probes (SEQ ID NO: 14) and (SEQ ID NO: 15) using TaKaRa terminal deoxynucleotidyl transferase and dTTP. The polyT-added probes were coated at separate sites on a single sheet of nylon membrane (4×0.4 cm) each in an amount of 0.5 µL. Ultraviolet ray at 312 nm was irradiated thereon for 2 minutes to immobilize them to prepare a detection strip.

Then, the following two kinds of reagents were prepared.

| Reagent (5) | 5 M | Sodium hydroxide |
|---|---|---|
|  | 0.05 M | EDTA |
| Reagent (6) | 0.01% | SDS |
|  | 1.8% | Sodium chloride |
|  | 1% | Sodium citrate |

To 10 µL of the sample amplified in the same manner as in Example 3 was added 10 µL of the reagent (5) and the mixture was stirred well and then left to stand for 5 minutes. To the sample solution were added 1 mL of the reagent (6) and a piece of the above detection strip, followed by shaking at a reaction temperature of 45° C. for 30 minutes to cause the reaction to proceed. Thereafter, alkaline phosphatase bound to streptoavidin was added thereto. Further, BCIP and NBT were added thereto. These cause the alkaline phosphatase bound to the samples bound to the respective probes on the detection strip to develop colors. The samples Nos. 1 to 8 were judged to have the genetic polymorphisms as shown in Table 7 below.

TABLE 7

|  | VDR Genetic Polymorphism | ApoE Genetic Polymorphism | ER Genetic Polymorphism |
|---|---|---|---|
| Sample No. 1 | Bb | 3/4 | xx |
| Sample No. 2 | BB | 4/4 | Xx |
| Sample No. 3 | bb | 3/3 | XX |

Effect of the Invention

According to the analytical method of the present invention, determination as to which remedy for osteoporosis a subject patient has higher sensitivity can be made with high probability before administration of the medicine so that selection of an appropriate medicine is possible. Therefore, inefficient therapy in which a medicine having poor therapeutic effect is administered for a long term can be avoided, so that the method of the invention is extremely useful for improving the QOL of the patient.

Using the detection reagent of the present invention, the three genes, i.e., VDR, ApoE and ER genes can be amplified simultaneously and the three genetic polymorphisms can be detected by a single operation using the amplified products. Further, since the genes are associated with osteoporosis, effective remedies for osteoporosis can be selected by use of the detection reagents based on a combination of genetic polymorphisms of the genes due to the results of detection of genetic polymorphisms.

Free Text of Sequence Listing

SEQ ID NOS: 1 and 2: Oligonucleotides designed to work as a primer for amplifying a fragment of VDR gene containing a polymorphism site.

SEQ ID NOS: 3, 4, 5 and 6: Oligonucleotide designed to work as a primer for amplifying a fragment of ApoE gene containing a polymorphism site.

SEQ ID NOS: 7, 8, and 9: Oligonucleotide designed to work as a primer for amplifying a fragment of ER gene containing a polymorphism site.

SEQ ID NOS: 10 and 11: Oligonucleotide designed to work as a probe for detecting a fragment of VDR gene containing a polymorphism site.

SEQ ID NOS: 12, 13, 18 and 19: Oligonucleotides designed to work as a probe for detecting a fragment of ApoE gene containing a polymorphism site.

SEQ ID NOS: 14, 15, 16 and 17: Oligonucleotides designed to work as a probe for detecting a fragment of ER gene containing a polymorphism site.

What is claimed is:

1. A method for determining the relative sensitivity of an individual to treatment of osteoporosis with vitamin D, estrogen, and vitamin K2, comprising determining whether an individual's vitamin D receptor genotype is B(+) or B(−), where B(+) represents the genotypes BB and Bb and B(−) represents the genotype bb, where B is a vitamin D receptor allele that is not cleaved with Bsm I in an intron region between exon 8 and exon 9 and b is a vitamin D receptor allele that is cleaved with Bsm I in an intron region between exon 8 and exon 9, determining whether the individual's estrogen receptor genotype is X(+) or X(−), where X(+) represents the genotypes XX and Xx and X(−) represents the genotype xx, where X is an estrogen receptor allele that is not cleaved with Xba in an intron region between exon 1 and exon 2 and x is an estrogen receptor allele that is cleaved with Xba in an intron region between exon 1 and exon 2, and determining whether the individual's apolipoprotein E genotype is 3(+), 3(−), 4(+), or 4(−), where 3(+) represents an apolipoprotein E 3/3 type, and 3(−) indicates an apolipoprotein E genotype other than apolipoprotein E 3/3 type, and 4 represents an apolipoprotein E4 allele, and (+) and (−) indicate the presence and absence, respectively, of the allele; wherein the combination of said individual's vitamin D receptor genotype, estrogen receptor genotype, and apolipoprotein E genotype is associated with the individual's relative sensitivity to vitamin D, estrogen and vitamin K2.

* * * * *

SEQUENCE LISTING

```
<160> NUMBER OF SEQ ID NOS:  25

<210> SEQ ID NO 1
<211> LENGTH: 20
<212> TYPE: DNA
<213> ORGANISM: Homo sapiens
<220> FEATURE:
<223> OTHER INFORMATION: Located on the 12th chromosome; a part of the
``` base sequence of vitamin D receptor gene.

<400> SEQUENCE: 1
gtgcaggcga ttcggtaggg                                                    20

<210> SEQ ID NO 2
<211> LENGTH: 20
<212> TYPE: DNA
<213> ORGANISM: Homo sapiens
<220> FEATURE:
<223> OTHER INFORMATION: Located on the 12th chromosome; a part of the
      base sequence of vitamin D receptor gene.

<400> SEQUENCE: 2
ccagcggaag aggtcaaggg                                                    20

<210> SEQ ID NO 3
<211> LENGTH: 16
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 3
ctgggcgcgg acatgg                                                        16

<210> SEQ ID NO 4
<211> LENGTH: 16
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 4
cccggcctgg tacact                                                        16

<210> SEQ ID NO 5
<211> LENGTH: 20
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 5
ctgggcgcgg acatggagga                                                    20

<210> SEQ ID NO 6
<211> LENGTH: 20
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 6
cccggcctgg tacactgcca                                                    20

<210> SEQ ID NO 7
<211> LENGTH: 20
<212> TYPE: DNA
<213> ORGANISM: Homo sapiens
<220> FEATURE:
<223> OTHER INFORMATION: Located on the 6th chromosome; a part of the
      base sequence of estrogen receptor gene.

-continued

<400> SEQUENCE: 7
gttccaaatg tcccagccgt                                              20

<210> SEQ ID NO 8
<211> LENGTH: 20
<212> TYPE: DNA
<213> ORGANISM: Homo sapiens
<220> FEATURE:
<223> OTHER INFORMATION: Located on the 6th chromosome; a part of the
      base sequence of estrogen receptor gene.

<400> SEQUENCE: 8
cctgcaccag aatatgtacc                                              20

<210> SEQ ID NO 9
<211> LENGTH: 21
<212> TYPE: DNA
<213> ORGANISM: Homo sapiens
<220> FEATURE:
<223> OTHER INFORMATION: Located on the 6th chromosome; a part of the
      base sequence of estrogen receptor gene.

<400> SEQUENCE: 9
cctgcaccag aatatgttac c                                            21

<210> SEQ ID NO 10
<211> LENGTH: 16
<212> TYPE: DNA
<213> ORGANISM: Homo sapiens
<220> FEATURE:
<223> OTHER INFORMATION: Located on the 12th chromosome; a part of the
      base sequence of vitamin D receptor gene.

<400> SEQUENCE: 10
caggcctgcg cattcc                                                  16

<210> SEQ ID NO 11
<211> LENGTH: 16
<212> TYPE: DNA
<213> ORGANISM: Homo sapiens
<220> FEATURE:
<223> OTHER INFORMATION: Located on the 12th chromosome; a part of the
      base sequence of vitamin D receptor gene.

<400> SEQUENCE: 11
caggcctgca cattcc                                                  16

<210> SEQ ID NO 12
<211> LENGTH: 14
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 12
aggacgtgcg cggc                                                    14

<210> SEQ ID NO 13
<211> LENGTH: 15
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 13
aggacgtgtg cggcc                                                                        15

<210> SEQ ID NO 14
<211> LENGTH: 16
<212> TYPE: DNA
<213> ORGANISM: Homo sapiens
<220> FEATURE:
<223> OTHER INFORMATION: Located on the 6th chromosome; a part of the
      base sequence of estrogen receptor gene.

<400> SEQUENCE: 14
gtgtggtcta gagttg                                                                       16

<210> SEQ ID NO 15
<211> LENGTH: 16
<212> TYPE: DNA
<213> ORGANISM: Homo sapiens
<220> FEATURE:
<223> OTHER INFORMATION: Located on the 6th chromosome; a part of the
      base sequence of estrogen receptor gene.

<400> SEQUENCE: 15
gtgtggtctg gagttg                                                                       16

<210> SEQ ID NO 16
<211> LENGTH: 16
<212> TYPE: DNA
<213> ORGANISM: Homo sapiens
<220> FEATURE:
<223> OTHER INFORMATION: Located on the 6th chromosome; a part of the
      base sequence of estrogen receptor gene.

<400> SEQUENCE: 16
tctggagttg ggatga                                                                       16

<210> SEQ ID NO 17
<211> LENGTH: 16
<212> TYPE: DNA
<213> ORGANISM: Homo sapiens
<220> FEATURE:
<223> OTHER INFORMATION: Located on the 6th chromosome; a part of the
      base sequence of estrogen receptor gene.

<400> SEQUENCE: 17
gtggtctaga gttggg                                                                       16

<210> SEQ ID NO 18
<211> LENGTH: 16
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 18
cagaagcgcc tggcag                                                                       16

<210> SEQ ID NO 19
<211> LENGTH: 16
<212> TYPE: DNA
<213> ORGANISM: Homo sapiens
<220> FEATURE:
<223> OTHER INFORMATION: Located on the 19th chromosome; a part of the
      base sequence of apolipoprotein E gene.

<400> SEQUENCE: 19
cagaagtgcc tggcag                                                           16

<210> SEQ ID NO 20
<211> LENGTH: 30
<212> TYPE: DNA
<213> ORGANISM: Homo sapiens
<220> FEATURE:
<223> OTHER INFORMATION: Located on the 12th chromosome; Oligonucleotide
      designed to act as primer for amplifying VDR gene fragment
      containing polymorphic site.

<400> SEQUENCE: 20
caaccaagac tacaagtacc gcgtcagtga                                            30

<210> SEQ ID NO 21
<211> LENGTH: 23
<212> TYPE: DNA
<213> ORGANISM: Homo sapiens
<220> FEATURE:
<223> OTHER INFORMATION: Located on the 12th chromosome; Oligonucleotide
      designed to act as primer for amplifying VDR gene fragment
      containing polymorphic site.

<400> SEQUENCE: 21
aaccagcggg aagaggtcaa ggg                                                   23

<210> SEQ ID NO 22
<211> LENGTH: 33
<212> TYPE: DNA
<213> ORGANISM: Homo sapiens
<220> FEATURE:
<223> OTHER INFORMATION: Located on the 6th chromosome; Oligonucleotide
      designed to act as primer for amplifying ER gene fragment
      containing polymorphic site.

<400> SEQUENCE: 22
ctgccaccct atctgtatct tttcctattc tcc                                        33

<210> SEQ ID NO 23
<211> LENGTH: 33
<212> TYPE: DNA
<213> ORGANISM: Homo sapiens
<220> FEATURE:
<223> OTHER INFORMATION: Located on the 6th chromosome; Oligonucleotide
      designed to act as primer for amplifying ER gene fragment
      containing polymorphic site.

<400> SEQUENCE: 23
tctttctctg ccaccctggc gtcgattatc tga                                        33

<210> SEQ ID NO 24
<211> LENGTH: 21
<212> TYPE: DNA
<213> ORGANISM: Homo sapiens
<220> FEATURE:
<223> OTHER INFORMATION: Located on the 19th chromosome; Oligonucleotide
      designed to act as primer for amplifying ApoE gene fragment
      containing polymorphic site.

<400> SEQUENCE: 24
cgggcacggc tgtccaagga g                                                     21

<210> SEQ ID NO 25
<211> LENGTH: 21
<212> TYPE: DNA
<213> ORGANISM: Homo sapiens
<220> FEATURE:

```
<223> OTHER INFORMATION: Located on the 19th chromosome; Oligonucleotide
      designed to act as primer for amplifying ApoE gene fragment
      containing polymorphic site.

<400> SEQUENCE: 25
cacgcggccc tgttccacga g                                              21
```